United States Patent [19]

Gabelman

[11] Patent Number: 5,132,217

[45] Date of Patent: Jul. 21, 1992

[54] START-UP OF CONTINUOUS BUTYRIC ACID FERMENTOR

[75] Inventor: Alan Gabelman, Landenberg, Pa.

[73] Assignee: Hercules Incorporated, Wilmington, Del.

[21] Appl. No.: 803,861

[22] Filed: Dec. 9, 1991

[51] Int. Cl.⁵ .................... C12P 7/52; C12R 1/145
[52] U.S. Cl. ..................... 435/141; 435/813; 435/842
[58] Field of Search ............ 435/141, 813, 842

[56] References Cited

U.S. PATENT DOCUMENTS 4,539,293  9/1985  Bergstrom et al. ............ 435/842
4,814,273  3/1989  Brumm et al. ................ 435/842

OTHER PUBLICATIONS

Japanese APS Abstract J62-267 (Jan. 6, 1987) Taiji Imanishi et al.
Japanese APS PBS J61-212282 (Sep. 1986) Shirai et al.

Primary Examiner—Herbert J. Lilling
Attorney, Agent, or Firm—Roy V. Jackson

[57] ABSTRACT

A process for starting up the continuous production of butyric acid by fermentation of a medium containing a starting amount of a nutrient substrate and a microorganism that converts the nutrient into butyric acid, that avoids an excess of nutrient in the fermentation broth and comprises the steps of (1) fermenting in a fermentor in batch style an amount of the medium that is substantially less than the working volume of the fermentor until the amount of the nutrient not yet converted is no more than a small fraction of the starting amount, (2) adding medium to the fermentor without removing any of the fermentation broth, until it contains approximately its working volume, then, (3) while continuing the addition, removing the fermentation broth containing the butyric acid product at a continuous rate that maintains a constant volume of medium in the fermentor, and thereafter maintaining continuous operation of the fermentation.

7 Claims, No Drawings

START-UP OF CONTINUOUS BUTYRIC ACID FERMENTOR

This invention relates to the production of butyric acid by the anaerobic fermentation of carbohydrates.

BACKGROUND OF THE INVENTION

Butyric acid is used in butter and rum flavors, and its ethanol ester (ethyl butyrate) is used in fruit flavors. Other esters of butyric acid are also used in flavors. The production of such natural flavor ingredients by fermentation has become a desirable alternative to their physical extraction from plants because it avoids the disadvantages of such extraction while retaining the recognized "natural" designation, based on the ruling by the FDA (21 CFR 101.22.a.3) that products of fermentation are considered natural provided that the starting substrate is a natural material such as glucose or sucrose.

The production of butyric acid by fermentation is well known. Often acetic acid is also produced in these fermentations; acetic acid and several of its esters (particularly ethyl acetate) are also of interest to the flavor industry. Usually a member of the genus Clostridium is used for the butyric acid fermentation, and the fermentation is conducted anaerobically. Substrates comprising sugars such as glucose, sucrose, and fructose, or carbohydrates that break down into such sugars are conventionally used, for example, in batch, semi-batch ("fed-batch") or continuous operations.

Fermentation processes that can produce butyric acid are described, for instance, in U.S. Pat. Nos. 4,539,293 and 4,814,273, and in an article published in *Appl. Microbiol. Biotechnol.* (34, 2, 172–77) 1990, by D. Michel Savin, D. R. Marchal, and J. P. Vandecasteele of the *Division Biotechnoloqie et Environnement, Institut Francais du Petrole*, that describes the metabolic behavior and production performance of *Clostridium tyrobutyricum* in a continuous culture.

U.S. Pat. No. 4,814,273 describes the fermentation in batch mode of a lactate salt to butyrate salt using *Butyribacterium methylotrophicum* (*B. methylotrophicum*), and following that fermentation with a second fermentation in the same mixture that converts a carbohydrate to lactic acid using a Lactobaccillus, preferably after removing the cells of the microorganism used in the first step. Productivity is usually higher with continuous operation (as suggested by the good results reported by Michel Savin et al. in the above literature publication), because unproductive downtime for repeatedly draining the fermentor, refilling the fermentor, and growing the culture is not required.

For continuous operation, the conventional arrangement is a chemostat, in which nutrient medium is fed to a stirred fermentor tank at a controlled rate and broth is removed at the same rate, so that the level in the fermentor remains constant. The dilution rate (expressed as liters.liter$^{-1}$.hr$^{-1}$, or simply hr$^{-1}$) must not exceed the maximum growth rate of the organism, and the formation of the desired product must be at least partially associated with the growth of the microorganism. Complex nutrient supplements (e.g., yeast extract) are conventionally used, as additives or in complex media compositions, to obtain a high yield of product, as in U.S. Pat. No. 4,814,273, although they may have some disadvantages; for example, these complex materials, which have variable compositions, can support growth of a wide variety of organisms, so that they render the fermentor more susceptible to unpredictable contamination. Furthermore, they usually are not completely soluble, which can lead to abrasion problems with heat exchangers, pumps, and fermentor agitator blades, and makes the medium unsuitable for sterilization by filtration, which is sometimes desirable to reduce energy costs or if the medium contains heat-labile components.

For these reasons a nutrient substrate essentially comprising a compound having a chemically definable structure, such as glucose or sucrose, and all other medium components having a chemically definable structure may be desirable, although the yield of the desired product may not be as high and small amounts of specific additional nutrients may have to be added.

The published disclosures of continuous fermentation work do not address the problems that are encountered in the conventional procedures used to start up a continuous butyric acid fermentation process. The fermentor is conventionally operated in batch mode until the concentration of the microorganism is sufficiently high, then addition of the fermentation medium (feedstock) and removal of the medium containing the butyric acid product (fermentation broth) at a continuous rate that maintains a constant volume of medium in the fermentor is continued. However, when feeding of the medium begins, it causes drastic changes in the established balance of the ingredients of the fermentation broth; the butyric and acetic acid concentrations typically decrease and the residual substrate concentration correspondingly increases. As much as several days may be required before the proper concentrations of the products in the medium are re-established. In a commercial process this transitory reduction in butyric acid yield can be very costly, and the presence of excessive substrate can interfere with downstream purification of the products.

There is clearly a need for a method of making a smooth transition from batch to continuous operating mode, without such undesirable changes in the established balance of the ingredients.

SUMMARY OF THE INVENTION

According to the invention, a process for the production of butyric acid by the fermentation of an aqueous medium containing a starting amount of a nutrient and a microorganism that converts the nutrient into butyric acid, involves a procedure for starting up the continuous butyric acid fermentor that eliminates this transition period, with no excess substrate or decrease in butyric acid concentration.

The process comprises a specific sequence of steps, starting with (1) fermenting in a fermentor an amount of the medium that is substantially less than the working volume of the fermentor, which in effect comprises growing the culture in batch mode as described above. Preferably the fermentor is filled only until it contain from 20% up to 60% of its working volume; and the fermentation is allowed to proceed in batch mode, without any additions of the nutrient substrate that would normally be made in fed-batch mode.

Step (2) is started when the amount of the nutrient not yet converted is no more than a very small selected fraction of the starting amount, preferably when the nutrient substrate concentration has been depleted to a level below 1 gram per liter while still maintaining the vitality of the microorganism, and involves adding medium to the fermentor without removing any of the fermentation broth, until it contains approximately its working volume, the rate of addition being not more than the maximum rate of conversion of the nutrient.

Then in step (3), while continuing the addition, the fermentation broth containing the butyric acid product is removed at a continuous rate that maintains a constant volume of medium in the fermentor, and thereafter continuous operation of the fermentation is maintained.

During step (2), while medium is added to the fermentor without removing any of the fermentation broth, the rate of addition (feedrate) may be set so that the dilution rate is equal to the desired dilution rate based on that final working volume in continuous mode. Alternatively and preferably, the dilution rate is set based on the initial volume, and the feedrate is increased as the level increases ("ramped" feedrate), so that the dilution rate remains approximately constant for maximum efficiency.

Once the fermentor working volume is reached, the step of removing the reaction broth mixture is started at a rate that maintains the volume of medium in the fermentor, whereby continuous operation is established. As mentioned above, the transition from batch to continuous operation occurs with no decrease in butyric acid concentration.

The invention can be successfully applied to any fermentation using a nutrient medium that is suitable for conventional fermentation that can be operated continuously, including those sometimes preferred for their high yield and using complex nutrient supplements such as yeast extract, but the following description and examples use nutrient media essentially comprising preferred examples of chemically definable compounds, namely, glucose and sucrose, to eliminate as far as possible uncontrolled variables and demonstrate the operability of the preferred methodology or best mode of the invention in the absence of extraneous and conventional factors that are available if desired but are not a part of the invention itself. Other nutrient compounds having definable structures, such as fructose and glycerol, are nutrients for members of the genus Clostridium that may be used in carrying out the invention, such as *Clostridium butyricum* (*C. butyricum*), *C. tyrobutyricum*, *C. pasteurianum*, *C. acetobutyricum*, *C. beijerinckii*, or *C. methylotrophicum*.

One of the parameters important to the successful implementation of the invention is the substrate concentration of the feed medium. Achievement of a smooth transition from batch to continuous mode is difficult at high substrate concentrations, which may make steady state continuous operation impractical. Preferably, the substrate concentration in the feed is such that the carbon is present at 14 to 17 g/l, and preferably at no more than 16 g/l. For example, glucose, which contains 40% carbon, and sucrose, with 42% carbon, give the preferred maximum carbon level of 16 g/l at concentrations of 40 g/l and 38 g/l respectively.

In the following examples, which further illustrate the invention, conventional additives including vitamins such as d-biotin, p-aminobenzoic acid (PABA), choline, folic acid, inositol, niacin, pantothenic acid, pyridoxine, riboflavin, and thiamine (most preferably, at least d biotin and PABA), and including minerals such as alkali metal and ammonium phosphates and sulfates of metals such as copper, magnesium or iron, are preferably used in the fermentation medium, to demonstrate the applicability of the invention to preferred conventional fermentation environments. In addition, the pH was conventionally maintained at about 6.2 by adding alkali metal hydroxide.

EXAMPLE 1

Start-up With a Glucose Medium at a Constant Feedrate

A 2.4 liter fermentor containing water was sterilized in place at 121° C. for 30 minutes, then the water was removed aseptically. One liter of the medium shown in Table 1 (except the ferrous sulfate) was prepared and transferred to the fermentor through a 0.2-micron sterilizing filter which had been autoclaved at 121° C. The ferrous sulfate was prepared separately as a concentrated solution, acidified to pH 2.5 by addition of citric acid, then transferred through a 0.2-micron sterilizing filter (which also had been autoclaved at 121° C.) into the fermentor. About 0.35 g/l of sterile antifoam was also added.

The stirring speed and temperature were maintained at 700 rpm and 35° C. respectively. Nitrogen was sparged throughout the fermentation at a rate of 0.1 standard liters per liter per minute. The fermentor was inoculated with 35 ml of a 12-hour culture of *Clostridium butyricum* ATCC 860 (American Type Culture Collection, Rockville, Md.). The pH was maintained at 6.2 by automatic addition of aqueous (450 g/l) potassium hydroxide.

After about 12 hours glucose was nearly depleted, the butyric acid concentration was 13 g/l, and the acetic acid concentration was 10 g/l. At that time feed of the medium shown in Table 1 (except ferrous sulfate) through a 0.2-micron sterilizing filter was begun at a feedrate of 180 ml/hr. As explained above, the ferrous sulfate was fed separately as a concentrated solution which had been acidified to pH 2.5 with citric acid. Sterile antifoam was also fed at a rate equal to approximately 0.35 grams per liter of medium feed. This fed-batch operation continued until the fermentor volume was 1.8 liters. At that time effluent removal began, and steady-state volume and dilution rate were established at 1.3 liters and 0.1 $hr^{-1}$ respectively. No appearance of residual glucose was observed, the butyric acid concentration did not drop below 13 g/l, and the acetic acid concentration did not drop below 10 g/l any time after the completion of the batch phase.

TABLE 1

| Glucose-based Fermentation Medium | |
|---|---|
| Component | Concentration, g/l |
| Glucose | 38.5 |
| Ammonium acetate | 5.0 |
| $KH_2PO_4$ | 0.5 |
| $K_2HPO_4$ | 0.38 |
| $MgSO_4.7H_2O$ | 0.2 |
| $FeSO_4.7H_2O$ | 0.1 |
| $NH_3H_2PO_4$ | 1.36 |
| p-aminobenzoic acid* | 0.01 |
| d-biotin | 0.001 |
| Softened water | balance |

*Potassium salt.

EXAMPLE 2

Start-up With a Sucrose Medium at a Constant Feedrate

The fermentor was prepared in exactly the same manner as in Example 1 except for the following:

the medium shown in Table 2 was used.

the magnesium sulfate and ferrous sulfate were prepared together as a concentrate, acidified to pH 2.5 with citric acid, then added to the fermentor separately from the rest of the medium.

the magnesium sulfate/ferrous sulfate concentrate was sterilized by autoclaving rather than by filtration.

pH was controlled with 500 g/l NaOH instead of 450 g/l KOH.

The fermentor was inoculated with 35 ml of a 12-hour culture of *Clostridium butyricum* ATCC 860. After about 12 hours sucrose was nearly depleted, the butyric acid concentration was 12 g/l, and the acetic acid concentration was 5 g/l. At that time feed of the medium shown in Table 2 was begun at a feedrate of 180 ml/hr. As explained above, the ferrous sulfate and magnesium sulfate were fed separately as a concentrated solution which had been acidified to pH 2.5 with citric acid. Sterile antifoam was also fed at a rate equal to approximately 0.4 grams per liter of fermentation medium. This fed-batch operation continued until the fermentor volume was 1.8 liters. At that time effluent removal began, and steady state volume and dilution rate were established at 1.3 liters and 0.1 $hr^{-1}$ respectively. No appearance of residual sucrose was observed, the butyric acid concentration did not drop below 12 g/l, and the acetic acid concentration did not drop below 5 g/l any time after the completion of the batch phase.

TABLE 2

| Sucrose-based fermentation medium | |
|---|---|
| Component | Concentration, g/l |
| Sucrose | 36.7 |
| Ammonium sulfate | 4.28 |
| $KH_2PO_4$ | 0.5 |
| $K_2HPO_4$ | 0.38 |
| $MgSO_4.7H_2O$ | 0.1 |
| $FeSO_4.7H_2O$ | 0.1 |
| p-aminobenzoic acid* | 0.01 |
| d-biotin | 0.001 |
| Softened water | balance |

*Potassium salt.

EXAMPLE 3

Start-up With a Sucrose Medium and the Feedrate Increased ("Ramped") With Increasing Fermentor Volume The fermentor was prepared and inoculated exactly as described in Example 2. Sucrose was nearly depleted after 12 hours, and the butyric and acetic acid concentrations were 12 and 5 g/l respectively. Medium feed was started at a rate of 100 ml/hr, i.e., at a dilution rate of 0.1 hr−1. This dilution rate was maintained approximately constant during the fed-batch phase by increasing the feedrate hourly based on current volume. For example, after one hour the volume was approximately 1.1 liters and the feedrate was increased to 110 ml/hr. The fermentor was operated in this manner until the volume was 1.8 liters, then broth removal began and the steady-state operating volume and dilution rate of 1.3 liters and 0.1 $hr^{31\ 1}$ respectively were established. No appearance of residual sucrose occurred, butyric acid concentration did not drop below 12 g/l, and acetic acid concentration did not drop below 5 g/l at any time after the completion of the batch phase.

I claim:

1. A process for the production of butyric acid by the fermentation of an aqueous medium containing a starting amount of a microorganism from the genus Clostridium and a nutrient for the microorganism consisting of a nutrient selected from the group consisting of fructose, glucose, glycerol and sucrose, that the microorganism is converting into butyric acid, comprising the steps of (1) fermenting in a fermentor an amount of the medium that is substantially less than the working volume of the fermentor until the amount of the nutrient not yet converted is no more than a small fraction of the starting amount, (2) adding medium to the fermentor without removing any of the fermentation broth, until it contains approximately its working volume, then, (3) while continuing the addition, removing the fermentation broth containing the butyric acid product at a continuous rate that maintains a constant volume of medium in the fermentor, and thereafter maintaining continuous operation of the fermentation; wherein the medium contains no more than 17 grams of carbon in the structure of the nutrient substrate per liter of the medium.

2. A process for the production of butyric acid as claimed in claim 1, in which during the step (2) of adding medium to the fermentor without removing any of the fermentation broth, the rate of addition is equal to the desired dilution rate based on the final working volume, which rate is not more than the maximum rate of conversion of the nutrient.

3. A process for the production of butyric acid as claimed in claim 1, in which during the step (2) of adding medium to the fermentor without removing any of the fermentation broth, the starting rate of addition is based on the initial volume in the fermentor, and is increased as the level increases, so that the dilution rate is maintained approximately constant.

4. A process for the production of butyric acid as claimed in claim 1, in which in step (1) the amount of the medium that is substantially less than the working volume of the fermentor is from 20% to 60% of the working volume of the fermentor.

5. A process for the production of butyric acid as claimed in claim 1, in which at the end of step (1) the amount of the nutrient not yet converted is less than 1 gram per liter while still sufficient to maintain the vitality of the microorganism.

6. The method claimed in claim 1 in which the nutrient substrate is selected from the group consisting of glucose or sucrose.

7. The method claimed in claim 1 in which the medium contains no more than 16 grams of carbon in the structure of the nutrient substrate per liter of the medium.

* * * * *

UNITED STATES PATENT AND TRADEMARK OFFICE
CERTIFICATE OF CORRECTION

PATENT NO. : 5,132,217
DATED : July 21, 1992
INVENTOR(S) : Alan Gabelman

It is certified that error appears in the above-identified patent and that said Letters Patent is hereby corrected as shown below:

Col. 5, line 51, "0.1 hr-1" should read "0.1 hr$^{-1}$".

Signed and Sealed this

Fifth Day of July, 1994

Attest:

BRUCE LEHMAN

Attesting Officer  Commissioner of Patents and Trademarks